(12) United States Patent
Morgan et al.

(10) Patent No.: US 10,039,667 B2
(45) Date of Patent: Aug. 7, 2018

(54) OCULAR IRRIGATION DEVICE AND METHOD

(71) Applicant: Mortan Inc., Missoula, MT (US)

(72) Inventors: Daniel T. Morgan, Freedom, WY (US);
Steven H. Bixby, Missoula, MT (US);
Zach T. Morgan, Missoula, MT (US);
Judy G. Devine, Missoula, MT (US)

(73) Assignee: MORTAN INC., Missoula, MT (US)

( * ) Notice: Subject to any disclaimer, the term of this patent is extended or adjusted under 35 U.S.C. 154(b) by 442 days.

(21) Appl. No.: 14/746,587

(22) Filed: Jun. 22, 2015

(65) Prior Publication Data
US 2016/0367398 A1 Dec. 22, 2016

(51) Int. Cl.
*A61F 9/00* (2006.01)
*A61M 3/02* (2006.01)

(52) U.S. Cl.
CPC ........... *A61F 9/0017* (2013.01); *A61M 3/027* (2013.01); *A61M 2210/0612* (2013.01)

(58) Field of Classification Search
CPC ..... A61F 9/0017; A61F 9/0008; A61H 35/02; A61M 2210/0612; A61M 3/027
USPC .......... 604/20, 290, 294–296, 298, 300, 301
See application file for complete search history.

(56) References Cited

U.S. PATENT DOCUMENTS

| | | | | |
|---|---|---|---|---|
| 2,524,720 A | * | 10/1950 | Watrous | A61F 9/0008 528/26 |
| 2,525,381 A | * | 10/1950 | Tower | A61F 9/0017 351/159.02 |
| 3,392,725 A | * | 7/1968 | Behney | A61D 7/00 351/159.02 |
| 3,664,340 A | | 5/1972 | Morgan | |
| RE28,873 E | * | 6/1976 | Morgan | A61F 9/0017 604/298 |
| 4,564,016 A | * | 1/1986 | Maurice | A61F 9/0017 604/20 |
| 4,798,599 A | * | 1/1989 | Thomas | A61H 35/02 604/19 |
| 5,387,201 A | * | 2/1995 | Fowler | A61M 3/0279 604/290 |
| 5,795,342 A | | 8/1998 | Shapiro et al. | |

(Continued)

OTHER PUBLICATIONS

"The Morgan Lens," MorTan Inc., retrieved from http://morganlens.com/, retrieved on Jan. 19, 2016, 125 pages (Parts I, II and III).

*Primary Examiner* — Susan Su
(74) *Attorney, Agent, or Firm* — Berg Hill Greenleaf & Ruscitti LLP

(57) ABSTRACT

An ocular irrigation device and method are provided including an ocular lens having selected structural features that facilitate flow of irrigation fluid to the eye through the ocular lens introduced by a source of irrigating fluid. The selected structural features achieve one or more objectives with respect to control of irrigation fluid so that selected portions of the eye and eyelids may be more effectively irrigated and treated. Control of the irrigation fluid by the invention includes variables of fluid flow characteristics to include control of flow velocity, flow volume, flow direction, and flow turbidity. Selected structural features of the ocular lens may address one or more of these variables alone or in selected combinations to provide an optimal method for treating a patient.

10 Claims, 13 Drawing Sheets

(56) References Cited

U.S. PATENT DOCUMENTS

| 8,262,715 B2* | 9/2012 | Wong, Jr. | A61F 7/12 |
| | | | 607/104 |
| 2006/0136022 A1* | 6/2006 | Wong, Jr. | A61B 3/165 |
| | | | 607/104 |

* cited by examiner

OCULAR IRRIGATION DEVICE AND METHOD

FIELD OF THE INVENTION

The invention relates to an ocular irrigation device and method for treatment of ocular ailments including trauma and disease, and more particularly, to a device and method in which an ocular treatment lens in preferred embodiments can control a number of treatment parameters including flow patterns and flow rates of irrigation fluid through and around the lens to optimize eye treatment.

BACKGROUND OF THE INVENTION

Ocular irrigation is a well-known procedure for treatment of eyes that are traumatized or otherwise have medical ailments. The Morgan Lens® is one well-known commercial ocular lens product. Currently, the Morgan Lens® is standard equipment in approximately 95% of hospital emergency rooms in the United States. The Morgan lens is capable of delivering a continuous flow of irrigation solution to an injured or compromised eye within seconds of being applied to the eye. There are many documented advantages of using an ocular irrigation device like the Morgan Lens® to handle a wide range of trauma and other ocular ailments.

The original Morgan Lens® is disclosed in the U.S. Pat. No. 3,664,340, and is hereby incorporated by reference herein. In short, the invention disclosed in this US patent includes an insertable and removable precision molded cup shaped ocular lens or eye shield. The lens more specifically is an integral, one piece unit including a cornea lens of a requisite diameter and convexity, and a surrounding peripheral and conformable rim. An opening is formed in the lens for attachment of a hollow stem or "chimney". The stem communicates with tubing which carries irrigation fluid so that the fluid may flow through the hollow stem to the area under the lens. One fundamental aspect of use of this ocular lens is that the irrigation fluid introduced causes the lens to float above the surface of the eye while continuously irrigating the eye. The irrigating solution creates a continuous film between the underside of the ocular lens and the exposed surface of the eye. The ocular lens is therefore capable of providing a continuous lavage to the cornea and conjunctiva, floating on the irrigating solution and not touching the cornea.

In many cases, the irrigating solution can provide instant relief to chemical or thermal burns, and may remove non-embedded foreign materials in the eye. Another aspect of the Morgan Lens® is that pressure applied to the cornea is minimized since the introduced fluid is capable of freely flowing outward beyond the peripheral edge of the ocular lens. This free flowing characteristic ensures the ocular lens can maintain its floating position above and away from contact with the cornea.

As time has progressed, ocular lenses like the Morgan Lens® find ever-increasing uses in hospitals and other treatment centers. In order to better service widely varying uses of ocular lenses, the below described invention was developed to address some existing and new needs in the field of ocular irrigation.

SUMMARY OF THE INVENTION

According to the invention in preferred embodiments of a device of the invention, an ocular irrigation device is provided including an ocular lens having selected structural features which facilitate flow of irrigation fluid to the eye through the ocular lens introduced by a source of irrigating fluid. One feature includes openings formed through the ocular lens that cause the introduced fluid to flow in selected different flow patterns or paths to achieve one or more objectives. Another feature includes grooves or ridges formed on an underside of the ocular lens, that is, the interior side or surface of the lens that faces the exposed surface of the eye when the ocular lens is installed. Yet another feature includes interior channels made in body of the lens that have openings which communicate with the underside of the lens, the upper surface of the lens, and/or the peripheral edge of the lens to selectively direct fluid flow in selected directions. Yet another feature includes increasing a curvature of a central convex portion or central dome of the ocular lens centered over the cornea of the eye when installed to increase the reservoir of fluid between the eye and lens. Yet another feature includes increasing a size of a conformable peripheral rim portion of the ocular lens to adjust fluid flow directed to corners of the eye or other areas more difficult to access with the irrigation fluid.

These new structural features can be incorporated alone or in selected combinations to achieve a desired irrigation objective. Irrigation objectives may be determined according to the particular trauma or other ailments an eye may have experienced.

According to one preferred embodiment of an irrigation system of the invention, a plurality of different types of ocular lenses can be provided in a kit, each with selected structural characteristics which may best treat patients with different types of injuries or diseases.

According to the invention in preferred embodiments of methods of the invention, selected types of ocular lenses are used to treat different types of injuries or diseases, each which may require a different irrigation protocol in order to best treat the situation at hand.

One preferred embodiment of the invention includes a plurality of openings formed through the body of the ocular lens. These openings help to facilitate flow of irrigating fluid between the upper surface of the ocular lens and the eyelid of the patient. In some circumstances, it may be desirable to provide a more thorough/quicker flushing of the eyelid tissue. Accordingly, some portion of the fluid flow will allow the lens to remain floating above the surface of the eye, while additional fluid is used to irrigate the eyelid tissue simultaneously. A flow rate of the irrigation fluid can be selected to increase or decrease the amount of irrigating fluid delivered to the affected eye to simultaneously irrigate both eyelid tissue and the eye. In one arrangement, there may be a set of four openings formed in the ocular lens, each being positioned at a quartile portion or quadrant of the lens. Various modifications to this preferred embodiment may include fewer or greater openings, as well as openings of different sizes and shapes. Some shapes specifically contemplated according to the invention include round, oval, triangular, and rectangular shaped openings.

Another preferred embodiment of the invention includes the use of a plurality of concentric interior annular irrigation ridges formed on the underside of the ocular lens. These annular irrigation ridges are incorporated to affect fluid flow and to ensure that an adequate reservoir of irrigating fluid will remain between the eye and lens. The annular ridges initially slow the flow rate of fluid around the peripheral edges of the ocular lens, and the ridges therefore help to retain an adequate fluid reservoir used as a cushion between the ocular lens and the eye. Alternatively, ridges can be formed on the upper surface of the ocular lens to increase irrigating fluid between the upper surface of the lens and the interior surface of the eyelid.

According to yet another preferred embodiment of the invention, it includes the use of a plurality of radially extending interior irrigation passageways. More specifically, the body of the ocular lens includes a plurality of interior passageways formed in the body and the passageways may generally extend from the centrally located stem or chimney radially outward to the peripheral rim of the ocular lens. These interior passageways may have openings that are exposed at the peripheral edge of the lens, and/or the interior passageways may have one or more openings formed on either the upper side or lower side of the ocular lens order to more directly transfer fluid flow to those areas.

According to yet another embodiment, the chimney or stem may include a concentric arrangement of tubes so that a portion of the irrigation fluid flows in one tube to the underside of the lens in the conventional manner, yet another portion of the irrigation fluid is directed through another tube to the interior irrigation passageways that communicate with the other tube. In this way, there is a separated but simultaneous flow of irrigating fluid to the underside of the lens as well as to other selected portions of the lens in order to more effectively irrigate selected portions of the eye or eyelid.

According to yet another preferred embodiment of the invention, it includes an additional or secondary stem that is also connected to a source of irrigating fluid so there are two distinct and separated sources of irrigating fluid that can be introduced to the underside of the lens. The size and location of this secondary stem/chimney may be selected in order to achieve the desired irrigating fluid pattern, such as to provide increased irrigation for one particular portion of the eye or eyelid, or for other purposes such as generally increasing the volume of fluid flow through the eye.

According to yet another preferred embodiment of the invention, it includes a convex body portion with an increased diameter and/or an increased convex curvature which therefore creates a larger sized open space between the surface of the eye and the underside of the ocular lens. This larger open space may therefore accommodate a greater reservoir of irrigation fluid between the eye and lens, and this additional fluid can also be used to alter fluid flow patterns. One particular objective for this embodiment may be to further increase the offset or float distance between the underside of the lens and the surface of the eye. Another objective for this embodiment may be to increase the flow rate of irrigation fluid in which the greater reservoir of irrigation fluid provides increased area for fluid to flow out from the peripheral edge of the ocular lens.

According to yet another embodiment of the invention, it includes an interior diffusing element for purposes of reducing the velocity of the incoming fluid flow from the irrigation stem and/or for purposes of changing the distribution pattern of the fluid as it contacts the eye. The diffusing element may be mounted to the interior surface of the ocular lens with a small flexible allowing the diffusing element to continually wobble or vibrate as irrigation fluid passed to enhance the turbidity of the fluid flow.

According to yet another embodiment of the invention, the ocular lens may further include an additional or secondary ocular lens in which the pair of lenses is placed in a stacked arrangement in which the secondary lens resides above the primary lens. The secondary lens is mounted to the stem at a predetermined height on the stem to separate the pair of lenses. The shape and size of the secondary lens may be substantially the same as the primary lens, or the secondary lens may have a slightly smaller diameter. Fluid from the stem is allowed to flow between the lenses in order to adjust fluid flow characteristics. The lenses may have sufficiently reduced thicknesses as compared to a single lens so that the pair may still fit comfortably within a patient's eye.

According to yet another embodiment of the invention, the ocular lens may include a modified irrigation stem with an interior surface that generates a vortex flow of irrigation fluid as it flows out from the irrigation stem. The vortex flow is created by helical arranged flutes or channels formed on the interior surface of the irrigation stem that causes fluid passing through the stem to travel in a helical/spiral fashion as the fluid exits from the stem. The vortex flow may improve turbulent flow of irrigation fluid for treatment to increase a dilution action.

According to yet another embodiment of the invention, the ocular lens may further include a peripheral border added to the peripheral edge of the lens. The peripheral border increases an overall diameter of the lens, but remains of a size that is still easily inserted in a patient's eye. This embodiment may be effective to distribute irrigation fluid more quickly to corners of the eye that may initially not receive an equal amount of irrigation fluid as compared to more interior or central exposed areas of the eye.

According to yet another embodiment of the invention, the ocular lens may further include one or more openings formed along the height of the irrigation stem such that a selected portion of the fluid flowing through the irrigation stem can be directed onto the upper surface of the lens. This embodiment may be advantageous if it is desired to provide more immediate flushing of the inner eyelids without the use of openings made in the body of the lens.

According to yet another embodiment of the invention, the ocular lens may further include a selected surface pattern formed on the interior or exterior surfaces of the lens, or both. The surface pattern may be a uniform or irregular group of surface features including protuberances, depressions, or combinations of both. One purpose of providing a surface pattern is to increase turbulence of the fluid flow thereby improving mixing action for dilution of caustic contaminants.

According to yet another embodiment of the invention, the ocular lens may further include a plurality of weakened areas defined by score lines adopted for creating openings in the lens to selectively control fluid flow characteristics. Types of score lines that may be adopted include round shaped score lines to create round openings in the body of the lens or channel shaped score lines to create channels or elongated openings in the body of the lens. These two examples are simply representative of the types of openings that may be made in the lens for purposes of fluid flow control. A user may choose to separate and remove selected portions of the lens defined within the score lines to create various flow patterns for fluid flow control.

Considering the above described features of the invention, in one particular aspect of the invention, it may also be considered an ocular lens, comprising: a body having a shape with a convex curvature; an irrigation stem connected to said body and having a passageway for fluid to pass through said irrigation stem and to enable the fluid to communicate with a lower surface of said body; and a body feature formed on said body, said body feature including at least one opening formed through said body and spaced from said irrigation stem. There are a number of optional features that may be considered in addition to this aspect of the invention, including any one of, or any combination of the following: wherein said at least one opening includes a plurality of openings spaced from one another on said body; said at least one opening has a shape selected from at least one of a circular shape, an oval shape, a triangular shape, or combinations thereof; said at least one opening includes a plurality of openings spaced from one another on said body, and said openings having uniform sizes and shapes; said at least one opening includes a plurality of openings spaced from one another on said body, and said openings having at least one of different sizes or shapes; at least one directional fin extending from an upper surface of said body; said body has a central convex portion and an outer circumferential body portion that surrounds said central convex portion, said circumferential body portion having a second different convex curvature; said at least one opening is formed in said central convex portion; said at least one opening is formed in said central convex portion and extends to said outer circumferential body portion, and/or said central convex portion has a first convex curvature and said circumferential body portion has a second different convex curvature.

According to another particular aspect of the invention, it may also be considered an ocular lens comprising: a body having a shape with a convex curvature; an irrigation stem connected to said body and having a passageway for fluid to pass through said irrigation stem and to enable the fluid to communicate with a lower surface of said body; and a body feature formed on said body, said body feature including at least one protuberance formed on said lower surface of said body. This particular aspect of the invention may further include any one of or any combination of the optional features described above according to the aforementioned particular aspect of the invention. Yet further, this aspect of the invention may optionally include wherein said at least one protuberance includes a plurality of concentric ridges formed on said lower surface. Protuberances may also be formed on the upper surface of the lens, and may include ridges, dimples, or combinations thereof. These types of upper surface features may help to hold and subsequently flush additional fluid between the upper surface of the lens and the interior surface of the eyelid.

According to yet another particular aspect of the invention, it may also be considered an ocular lens comprising: a body having a shape with a convex curvature; an irrigation stem connected to said body and having a passageway for fluid to pass through said irrigation stem and to enable the fluid to communicate with a lower surface of said body; and a body feature formed on said body, said body feature including at least one depression formed on an upper surface of said body, a lower surface of said body, or combinations thereof. This particular aspect of the invention may further include any one of or any combination of the optional features described above according to the aforementioned particular aspect of the invention. Yet further, this aspect of the invention may optionally include: wherein said at least one depression includes a plurality of concentric grooves formed on said lower surface.

According to yet another particular aspect of the invention, it may also be considered an ocular lens comprising: a body having a shape with a convex curvature; a primary irrigation stem connected to said body and having a passageway for fluid to pass through said irrigation stem and to enable the fluid to communicate with a lower surface of said body; and a body feature formed on said body, said body feature including at least one of: (i) at least one interior passageway formed through said body, said at least one interior passageway having a first end communicating with said irrigation stem and a second opposite end having an opening to allow fluid to pass from said irrigation stem into said interior passageway and out through said opening; (ii) a secondary irrigation stem spaced from said primary irrigation stem, said secondary irrigation stem connected to an upper surface of said body and having a secondary passageway for fluid to pass through said secondary irrigation stem and to communicate with said lower surface of said body; (iii) a diffusing element secured to said lower surface of said body; (iv) a secondary lens disposed above and spaced from said body; (v) a surface pattern formed on at least one of said upper or lower surfaces of said body; (vi) at least one score line formed on said body, said score line defining an opening or channel to be formed on said body by separating a portion of said body that resides within said score line, or (vii) one or more openings formed along a height of said irrigation stem such that a selected portion of the fluid flowing through said irrigation stem can be directed onto an upper surface of the lens. This particular aspect of the invention may further include any one of or any combination of the optional features described above according to the aforementioned particular aspect of the invention. Yet further, this aspect of the invention may optionally include: wherein said at least one interior passageway includes a plurality of interior passageways extending radially away from said irrigation stem; said at least one interior passageway has said opening formed at a peripheral edge of said body; said at least one interior passageway has said opening formed on at least one of (i) a peripheral edge of said body, (ii) said upper surface of said body, (iii) said lower surface of said body, or (iv) combinations thereof.

According to yet another particular aspect of the invention, it may also be considered a method of irrigating an eye by use of an ocular irrigation device to improve predetermined fluid flow irrigation parameters, said method comprising: providing an ocular lens including a convex shaped body and a primary irrigation stem connected to said body, said irrigation stem having a passageway for irrigation fluid to pass through said primary irrigation stem; determining at least one irrigation parameter to be improved, said at least one irrigation parameter being defined by fluid flow characteristics of fluid flowing through said ocular lens, said at least one irrigation parameter including at least one of fluid velocity, fluid volume, fluid direction, fluid turbidity, or combinations thereof; and selecting a feature to be incorporated on said ocular lens to achieve an improvement associated with at least one selected parameter. This particular aspect of the invention may further include any one of or any combination of: wherein said irrigation parameter is fluid velocity or fluid turbidity, and said selected feature is at least one depression or protuberance formed on said lens to slow velocity of fluid flow as it passes through said lens or to increase fluid turbidity; wherein said irrigation parameter is fluid direction and said selected feature is at least one interior passageway formed in said lens to re-direct fluid flow through said passageway in a direction of said passageway; wherein said irrigation parameter is fluid volume and said selected feature is a secondary irrigation stem spaced from said primary irrigation stem, said secondary irrigation stem connected to an upper surface of said body and having a secondary passageway for fluid to pass through said secondary irrigation stem to increase fluid volume delivered to the eye wherein said irrigation parameter is fluid speed or fluid turbidity, and said selected feature is a diffusing element secured to a lower surface of said body to increase turbidity or to slow fluid speed, or both; wherein said irrigation parameter is fluid direction or fluid turbidity, and said selected feature is a secondary lens disposed above and spaced from said body; wherein said irrigation parameter is fluid speed or fluid turbidity, and said selected feature is a surface pattern formed on at least one of said upper or lower surfaces of said body to slow speed of the fluid or to increase fluid turbidity, or both, or wherein said irrigation parameter is fluid direction or fluid turbidity, and said selected feature is at least one score line formed on said body, said score line defining an opening or channel to be formed on said body by separating a portion of said body that resides within said score line.

According to yet another aspect of the invention, it may be considered an ocular lens, comprising a body having a shape with a convex curvature; and an irrigation stem connected to said body and having a passageway for fluid to pass through said irrigation stem and to enable the fluid to communicate with a lower surface of said body, said irrigation stem having a helical arranged interior channel form on an interior surface of said irrigation stem to induce a vortex type flow patter of the fluid.

According to yet another aspect of the invention, it may be considered an ocular lens, comprising: a body having a shape with a convex curvature; a peripheral border integral with a peripheral edge of said body to increase a size of said body; and an irrigation stem connected to said body and having a passageway for fluid to pass through said irrigation stem and to enable the fluid to communicate with a lower surface of said body. According to this aspect, another feature of the invention includes wherein said body has a first thickness, and said peripheral border has a second thinner thickness.

According to yet another aspect of the invention, it may be considered an ocular lens, comprising: a body having a shape with a convex curvature; a plurality of weakened areas formed on said body and especially adapted for creating openings in the lens to selectively control fluid flow characteristics; and an irrigation stem connected to said body and having a passageway for fluid to pass through said irrigation stem and to enable the fluid to communicate with a lower surface of said body.

According to this aspect, another feature of the invention includes wherein said plurality of weakened areas are defined by corresponding score lines, and portions of said body within said score lines are separated from said body along said score lines.

The above described the features of the invention are described in greater detail below in the detailed description of the drawings. Other features and advantages of the invention will become apparent from a collective review of the detailed description and drawings.

DETAILED DESCRIPTION

Figure 1:
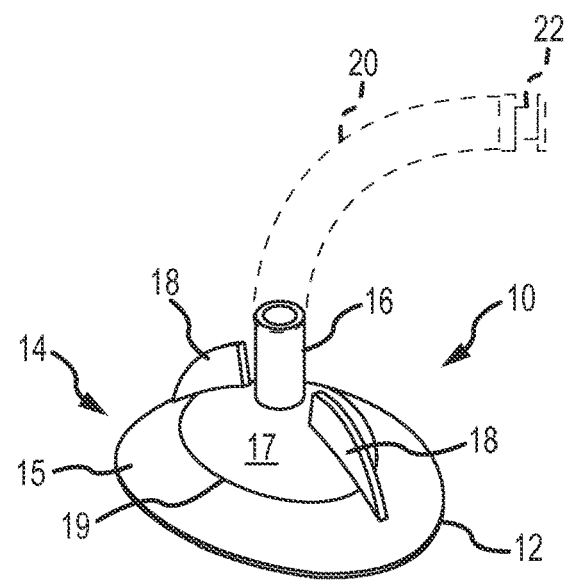
FIG. 1 is a perspective view of a prior art ocular lens.
Figure 2:
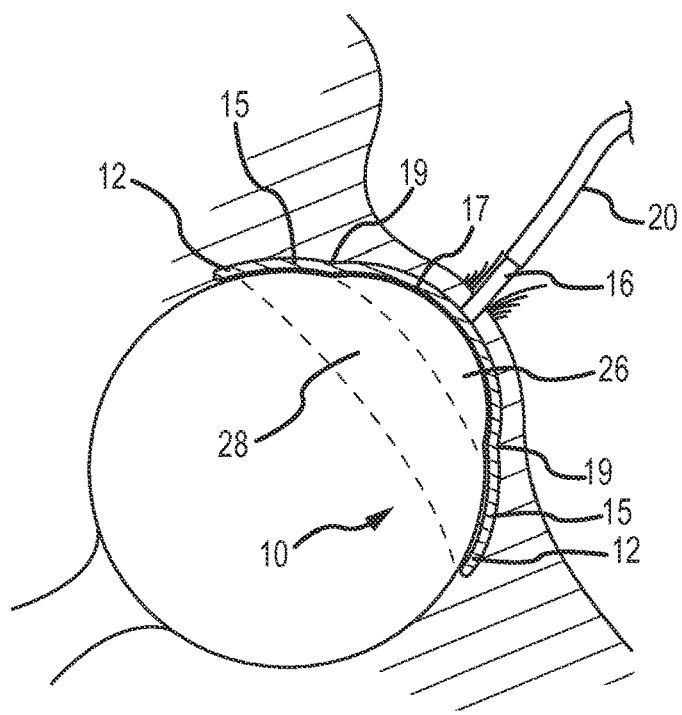
FIG. 2 is an enlarged cross-section of the prior art ocular lens of FIG. 1 showing the lens installed over an eye to be treated.
Figure 3:
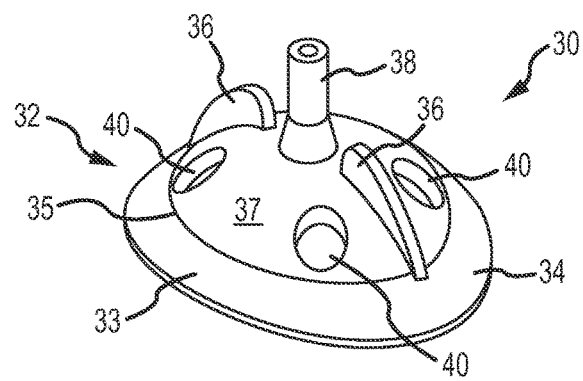
FIG. 3 is a perspective view of an ocular lens, according to a first embodiment of the invention.

FIG. 1 illustrates a prior art ocular lens 10, such as the Morgan Lens®. The lens 10 has a generally convex curvature and is especially sized and configured to be secured over the eye of a patient for irrigation of the eye. The lens 10 generally includes a conformable peripheral rim 12, and a convex shaped body 14. Referring also to FIG. 2, the body 14 may be further defined as having an outer circumferential body portion 15 with a first convex curvature, and a central convex portion or dome 17 having a second greater convex curvature. The outer circumferential body portion 15 is especially adapted for matching a size and curvature of the sclera 28 of the eye, while the central dome 17 is especially adapted for matching a size and curvature of the cornea 26 of the eye. The area of the lens where a transition or change occurs between the curvatures of portions 15 and 17 is shown as transition line 19. Other structural features of the prior art lens 10 include a pair of directional fins or flanges 18 that may be used to keep the lens centered over the eye in which the directional fins 18 protrude from the lens between the superior and inferior eyelids when the lens is installed. A fluid transfer stem or irrigation chimney 16 is generally centered within the dome 17, and the irrigation stem is used to deliver fluid to the interior or underside of the lens when installed. Irrigation tubing 20 and associated adapters or fittings 22 are used to interconnect an irrigation source, such as bag of irrigation fluid (not shown), to the fluid transfer stem 16. The stem 16 is illustrated having a larger diameter than the tubing 20 such that the end of the tube is placed within the opening of the stem for a friction fit; however, this arrangement could be reversed in which the stem has a smaller diameter and the end of the tube 20 is slipped over the stem 16 for a friction fit. In either case, the tube 20 and stem 16 provide an uninterrupted passageway between the fluid source and the interior or underside of the ocular lens 10.

Referring to FIG. 2, fluid is delivered such that the ocular lens floats above the surface of the eye and this figure is intended to illustrate a small gap or space creating a fluid reservoir between the interior or underside of the ocular lens and the surface of the eye. Other details of this prior art ocular lens are described in the U.S. Pat. No. 3,664,340.

An ocular lens provides therapeutic benefits in two general mechanisms of action, namely, dilution and flushing/rinsing. With respect to dilution, this mechanism of action may be required to dilute a caustic irritant introduced to the eye. With respect to flushing/rinsing, this may be required to remove a caustic substance, to clean the eye from other contaminants, or to introduce therapeutic fluids.

The prior art device shown in FIGS. 1 and 2 has proven to be a simple, yet reliable and effective system for irrigation of the eye. The construction of the device shown in these figures has been used for many decades in literally thousands of medical procedures which have successfully irrigated eyes for many patients.

According to the present invention, further developments and refinements of the prior art ocular lens design are disclosed herein in which different objectives may be achieved with the corresponding design changes. One general objective for the disclosed design changes is to provide selectively variable flow patterns of irrigation fluid so that targeted portions of the eye and eyelids may be more effectively irrigated or otherwise treated. Another general objective for the disclosed design changes is to provide selectively variable flow rates of irrigation fluid to provide even further options for caregivers in terms of how a treatment is to be conducted. In some circumstances, such as severe eye trauma or chemical or biological irritants introduced into the eye, it may be necessary to provide a relatively high flow rate of irrigating fluid for a period of time. In other circumstances, for example, incremental introduction of medicaments such as antibiotics, the flow rate of irrigating fluid may be required to be much slower and applied over a longer period of time. In either example situation, the embodiments of the present invention provide additional options for caregivers in order to selectively vary both the flow patterns of irrigation fluid as well as the flow rates of the irrigation fluid.

Figure 4:
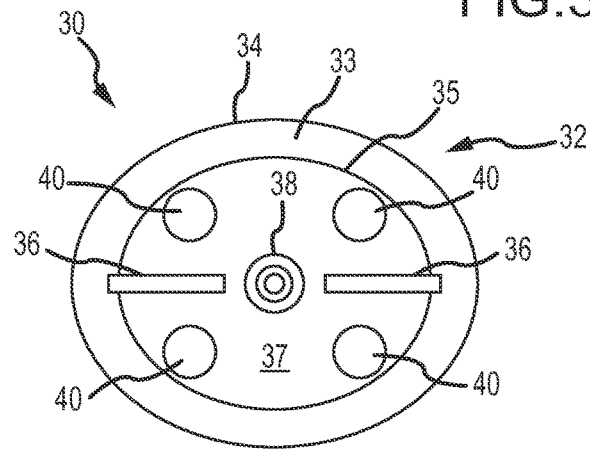
FIG. 4 is a top plan view of FIG. 3.
Figure 5:
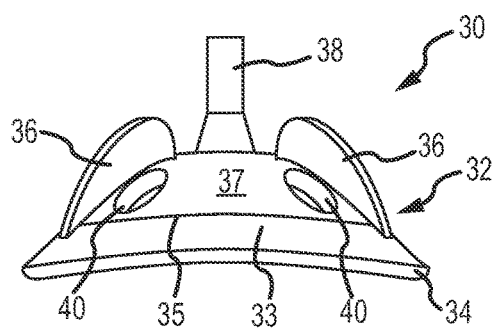
FIG. 5 is a front side elevation view of FIG. 3.
Figure 6:
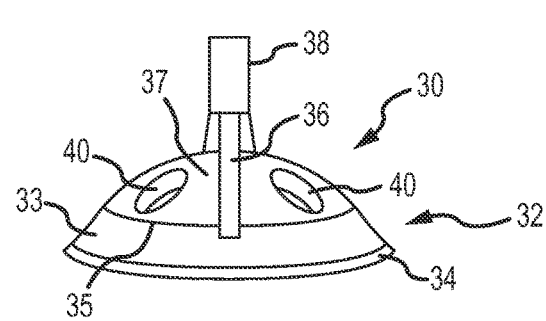
FIG. 6 is a right side elevation view of FIG. 3.
Figure 7:
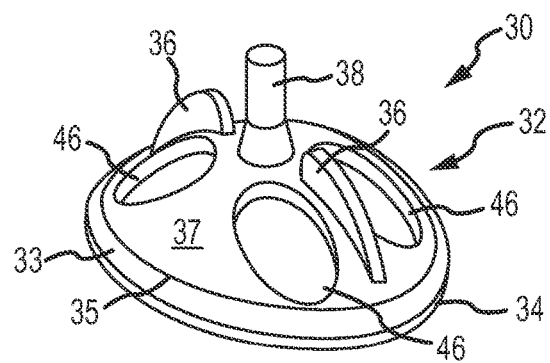
FIG. 7 is a perspective view of an ocular lens, according to another embodiment of the invention.
Figure 8:
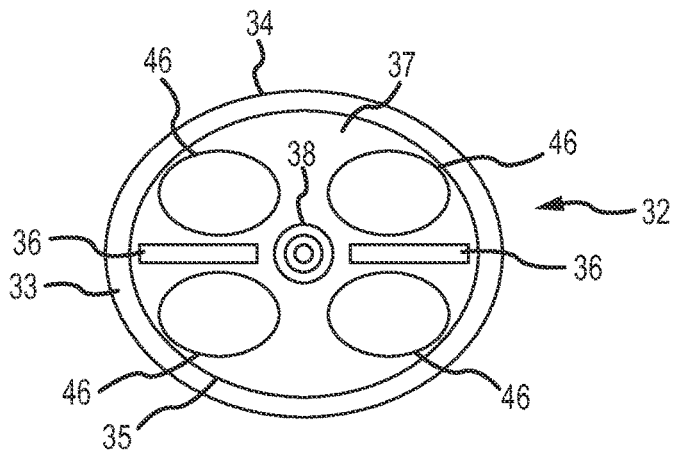
FIG. 8 is a top plan view of FIG. 7.
Figure 9:
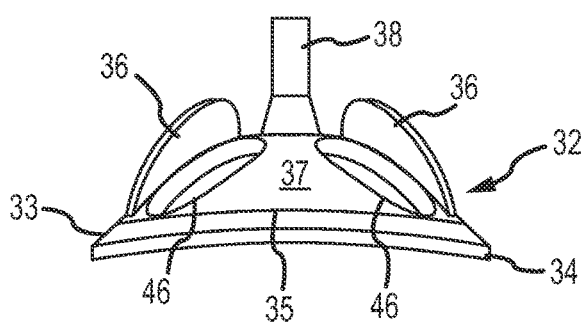
FIG. 9 is a front side elevation view of FIG. 7.
Figure 10:
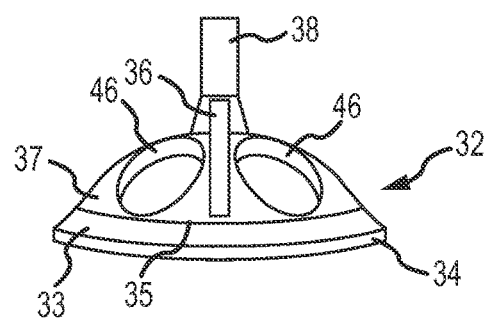
FIG. 10 is a right side elevation view of FIG. 7.
Figure 11:
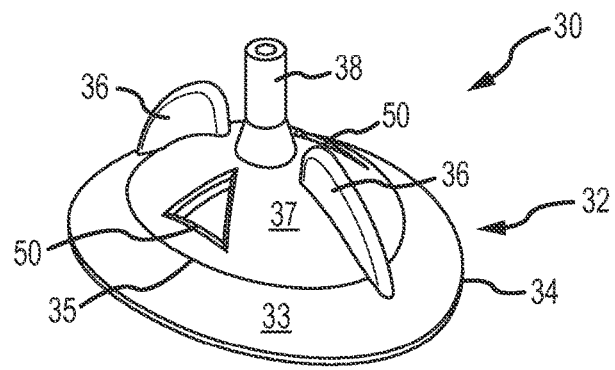
FIG. 11 is a perspective view of an ocular lens, according to another embodiment of the invention.
Figure 12:
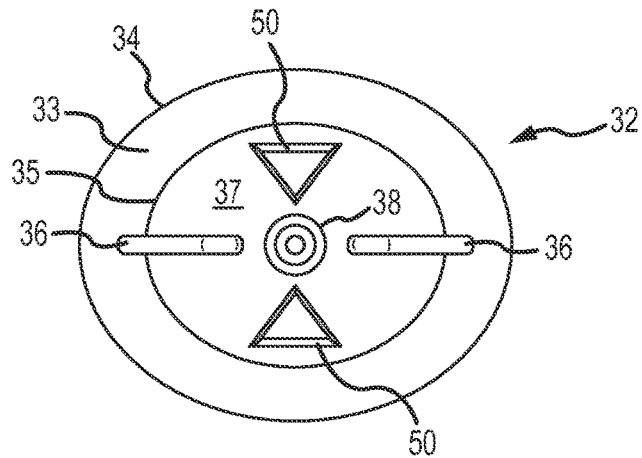
FIG. 12 is a top plan view of FIG. 11.
Figure 13:
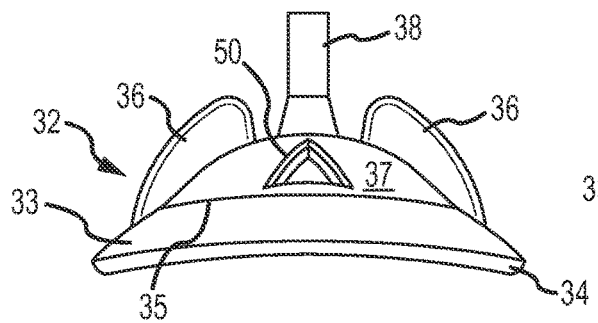
FIG. 13 is a front side elevation view of FIG. 11.
Figure 14:
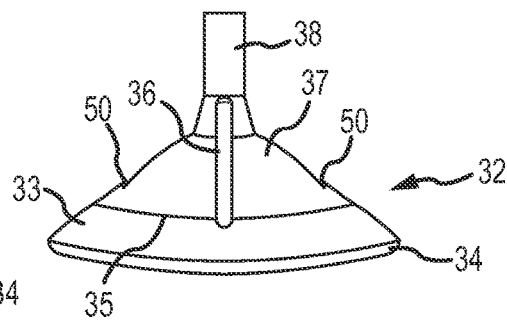
FIG. 14 is a right side elevation view of FIG. 11.
Figure 15:
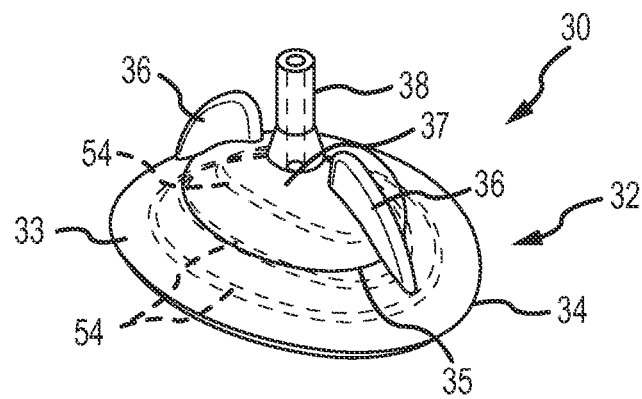
FIG. 15 is a perspective view of an ocular lens, according to another embodiment of the invention.
Figure 16:
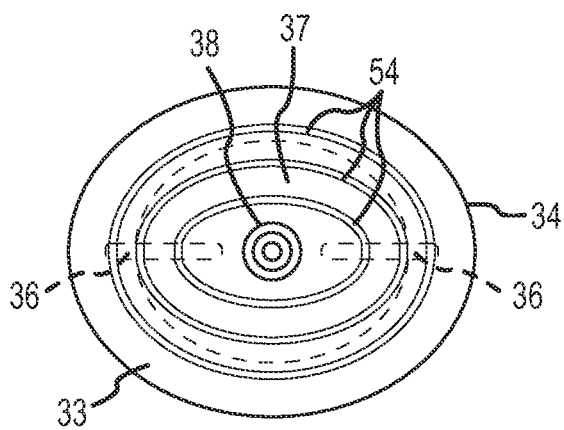
FIG. 16 is a bottom plan view of FIG. 15.
Figure 17:
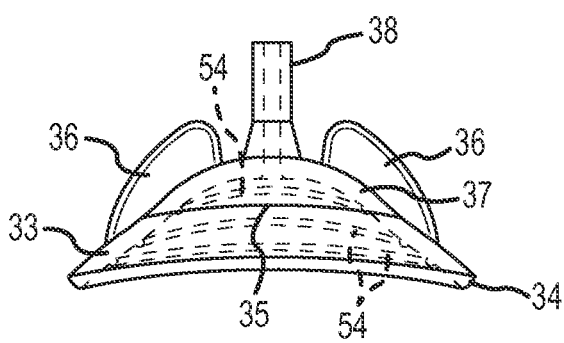
FIG. 17 is a front side elevation view of FIG. 15.
Figure 18:
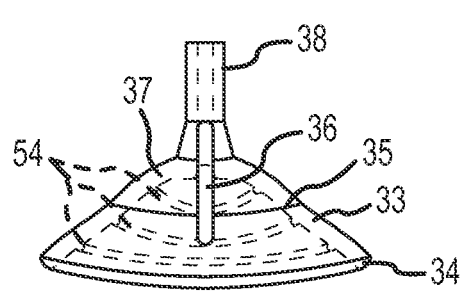
FIG. 18 is a right side elevation view of FIG. 15.
Figure 19:
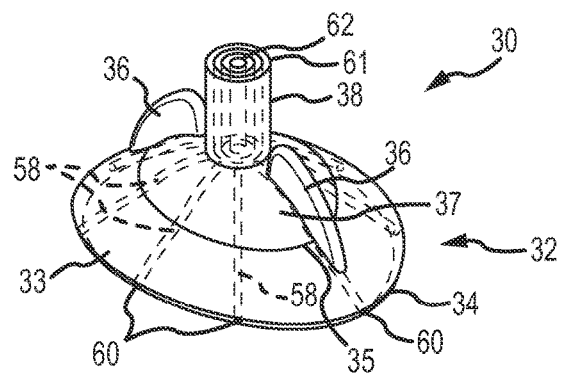
FIG. 19 is a perspective view of an ocular lens, according to another embodiment of the invention.
Figure 20:
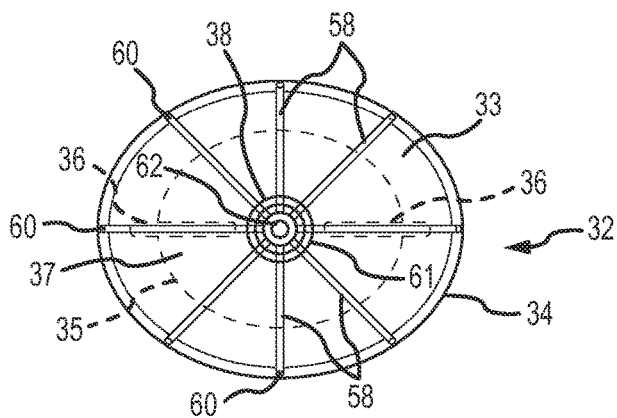
FIG. 20 is a bottom plan view of FIG. 19.

Referring to FIGS. 3-6, one preferred embodiment of the device of the invention shows an ocular lens 30 that is similar in some respects to the prior art but has added structural features. More specifically, lens 30 like lens 10 includes a conformable peripheral rim 34, a body 32, directional fins 36, as well as and an irrigation stem or chimney 38. FIGS. 3-6 also show other features of the lens including a central convex portion 37 with a first convex curvature, an outer circumferential body portion 33 that surrounds the central convex portion 37, the circumferential body portion 33 having a second different convex curvature, and a transition indicated at transition line 35. The curvature of the central convex portion is shown as being greater than the curvature of the circumferential body portion similar to the prior art. However, the lens 30 includes new features according to the invention shown as a plurality of irrigation openings 40 formed in the body 32 of the lens. Referring also to FIGS. 4-6, the irrigation openings 40 are shown as being spaced from one another around a periphery of the lens, in which there is one irrigation open 40 founded each quartile or quarter section of the lens 30. The openings 30 are each shown as having a uniform round shape and being located within the portion of the body 32 of the lens that resides over the cornea when installed. However, it should be understood that the number of openings, the size of the openings, their general spacing with one another, as well as their specific configuration on the body of the lens may be modified to provide the desired irrigation effect.

In general, the ocular lens design shown in FIGS. 3-6 enable an increased flow rate of irrigation fluid since the openings 40 provide additional flow path opportunities for the irrigation fluid. In the prior art design, irrigating fluid must initially make its way around the outer peripheral edges of the lens and during that time, only the cornea is being flushed. Therefore, the general concept of providing one or more openings in the body of the lens allows irrigating fluid to reach the inside surfaces of the eyelids more quickly. Another advantageous effect of the openings 40 is that an increased volume of irrigation fluid can be provided without materially affecting the pressure of the lens against the eye, since fluid is able to flow both under and over the lens surfaces simultaneously. In any event, adequate flow is still provided under the lens so that the lens maintains its floating position above the eye to prevent contact with the eye. Another advantage of providing openings through the lens is that this configuration may provide a more thorough flushing action since the fluid may have a greater velocity when it reaches the surfaces of the inner eyelid. Further, the presence of the openings may create greater turbulence in the fluid flow that may also enhance both the dilution and flushing actions.

Referring to FIGS. 7-10, another preferred embodiment is illustrated in which the ocular lens 30 has a plurality of openings 46 that are of greater size than the openings 40 shown in FIGS. 3-6. More specifically, the openings 46 formed in the body of the lens 32 have oval shapes and occupy a greater surface area on the body 32 of the lens. The embodiment shown in FIGS. 7-10 may be advantageous for use when it is necessary to provide an even greater flow rate of irrigation fluid in order to more quickly flush both cornea tissue and eyelid tissue. Although the surface area of the lens may be significantly reduced in this embodiment, adequate flow will still be generated radially outward beyond the peripheral rim 34 enabling the lens 30 to remain in a floating position above the eye.

Referring to FIGS. 11-14, another embodiment is illustrated in which openings in the body of the lens are provided in a different shape and configuration. More specifically, this embodiment illustrates two triangular shaped openings 50 formed in the body 32, one opening provided on both opposing sides of the lens as illustrated. Given an equal flow of irrigation fluid through the irrigation stem 38, it can be presumed there will be less irrigation fluid initially introduced to the eyelids as compared to the embodiment of FIGS. 7-10, however the openings 50 will still provide a more immediate flushing of eyelid tissue as compared to the prior art design.

Referring to FIGS. 15-18, yet another embodiment is illustrated with features formed on the interior or underside of the body 32. These features are illustrated as a plurality of annular interior ridges 54. The ridges 54 are formed in a concentric pattern in which three concentric ridges 54 are centered on the interior surface of the body 32. As compared to a smooth interior lens surface, the presence of the annular ridges 54 will generally slow the velocity of the irrigation fluid and thereby disrupt the irrigation solution so it does not flow in a laminar or uniform manner over the surface of the eye. The ridges 54 have multiple potential purposes for selectively adjusting an ocular irrigation procedure. One purpose is to increase the turbidity or turbulence of the irrigation fluid flow. Increased turbulence for the flow may provide a more immediate and efficient dilution action on chemical or biological irritants. Another purpose may be to maintain increased turbulence during an extended lavage procedure which may enhance overall circulation of the irrigation fluid with all parts of the eye. Yet another purpose may be to slow the velocity of the fluid flow which may serve to improve irrigation fluid circulation in some procedures in which it is desired to generally slow the velocity of the fluid flow. Greater or fewer ridges 54 can be provided in order to adjust fluid flow characteristics. The height at which the ridges protrude from the interior surface of the body of the lens can also be adjusted to adjust fluid flow characteristics. In another aspect of this embodiment, it is also contemplated that the annular interior ridges 54 may be reconfigured in other shapes to direct fluid flow to regions of the eye where less fluid typically flows, or where a caregiver may wish to especially concentrate an increased flow of fluid. For example, the ridges 54 could be reconfigured so that they are disposed in a combined group of arcuate members, parallel members, or combinations thereof that specifically channel irrigation fluid to selected portions of the eye.

In another aspect of the invention according to the embodiment of FIGS. 15-18, the ridges 54 may represent grooves or a selected combination of ridges and grooves. Like ridges, the provision of grooves may also be used to direct fluid flow in a desired manner to best accomplish the desired irrigation procedure to be conducted on a patient. In a broad sense of the invention, the term "protuberance" can be used to describe the ridges 54 or other features that that may protrude from the surface of the ocular lens, such as bumps, knobs, juts, jags, protrusions, and others. In another broad aspect of the invention, the term "depression" can be used to describe grooves or other features that may extend into the body such as a cut, slit, channel or furrow.

Figure 21:
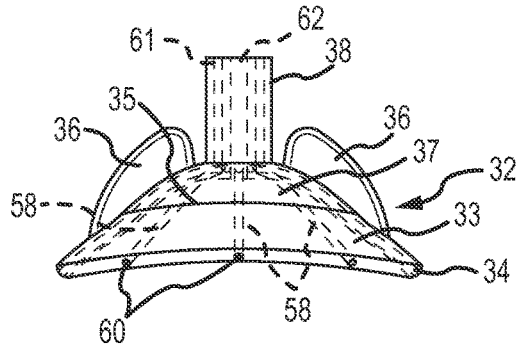
FIG. 21 is a front side elevation view of FIG. 19.
Figure 22:
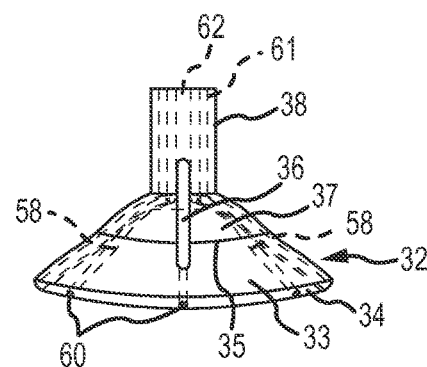
FIG. 22 is a right side elevation view of FIG. 19.
Figure 23:
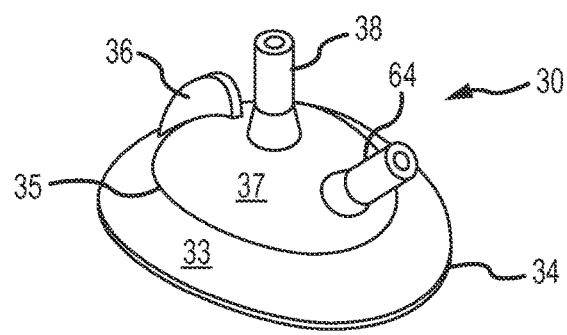
FIG. 23 is a perspective view of an ocular lens, according to another embodiment of the invention.
Figure 24:
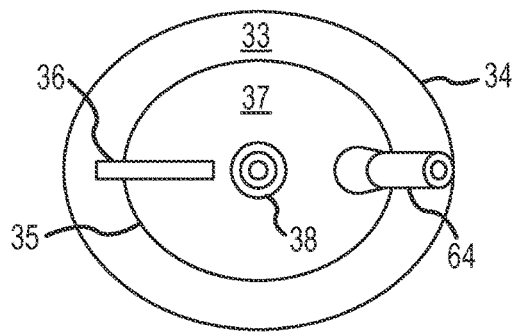
FIG. 24 is a top plan view of FIG. 23.
Figure 25:
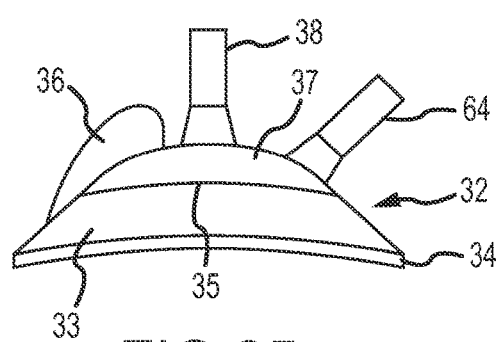
FIG. 25 is a front side elevation view of FIG. 23.
Figure 26:
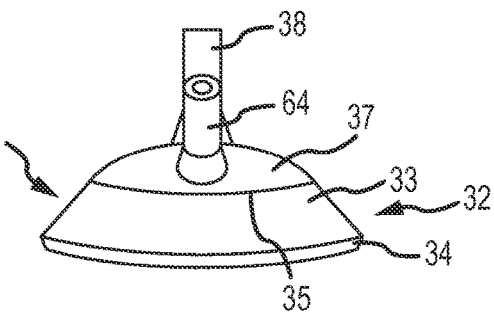
FIG. 26 is a right side elevation view of FIG. 23.
Figure 27:
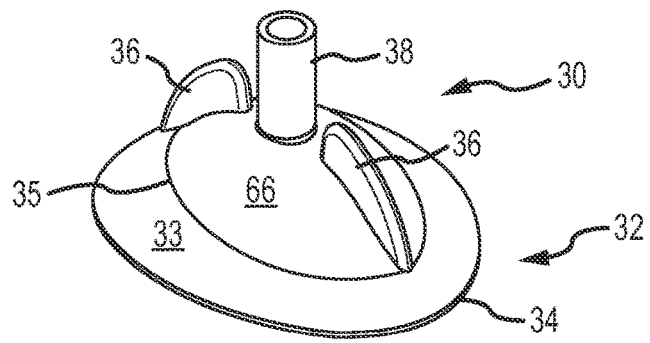
FIG. 27 is a perspective view of an ocular lens, according to another embodiment of the invention.
Figure 28:
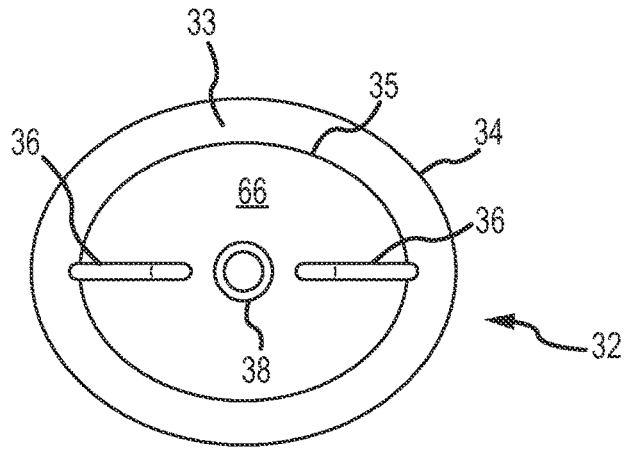
FIG. 28 is a top plan view of FIG. 27.
Figure 29:
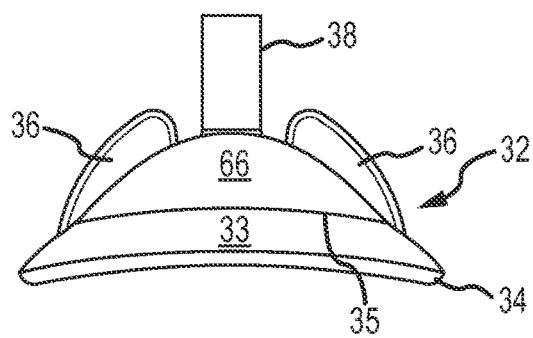
FIG. 29 is a front side elevation view of FIG. 27.
Figure 30:
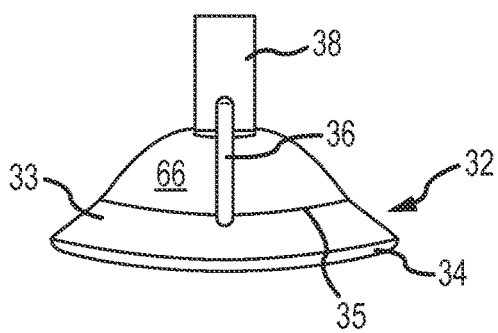
FIG. 30 is a right side elevation view of FIG. 27.

Referring to FIGS. 19-22, yet another embodiment is illustrated with other features formed incorporated in the body 32 of the ocular lens 30. These features are illustrated as a plurality of radially extending interior fluid passageways 58. The passageways 58 each communicate with the irrigation stem 38, so that fluid may flow directly from the stem into the passageways 60. In this regard, the stem 38 may be divided internally with multiple concentric tubes such that one tube communicates with the passageways 58, and another tube directs fluid to the interior surface of the body of the lens in the conventional manner. As best seen in the plan view of FIG. 20, one annular interior tube 61 is provided within the stem 38 that communicates with the passageways 58, while a most interior tube 62 communicates directly with the interior surface of the body of the lens. As best seen in FIGS. 21-22, the fluid passageways 58 extended to the peripheral rim 34 to form openings 60 that allows irrigation fluid to be conveyed directly to the peripheral edge of the lens. As with the ridges 54, the fluid passageways 58 have multiple potential purposes. One purpose of the passageways 58 is to provide some sustained fluid flow directly to the fornices of the eye. Another purpose of the passageways 58 is to reduce or otherwise control the rate of fluid flow through the eye in which flow velocity is generally decreased as compared to fluid flow through a stem that is not divided into separate interior annular tubes. Another purpose for the passageways 58 may be to direct fluid flow not only to the fornices of the eye, but to other areas of the eye in which other openings may be formed in the passageways 58 to directed fluid flow directly to other areas of the eye. For example, some or all of the fluid passageways 58 may terminate with openings 60 located along the periphery of the body as illustrated, or openings 60 located along the interior surface of the body, or openings 60 located along the exterior surface of the body, or combinations thereof.

Referring to FIGS. 23-26, yet another embodiment is illustrated in which a secondary irrigation stem 64 is secured to the body 32 of the lens. One purpose for the secondary irrigation stem 64 is to increase fluid flow to the eye, as may be required for certain traumatic events in which the eye requires an immediate irrigation of a substantial amount of irrigation fluid, or an increased flow of irrigation fluid over a sustained period. For configurations in which connected IV tubing 20 has a greater diameter than either the Luer lock connection or the irrigation stem 38, the irrigation stem can be the limiting flow element because of its smaller diameter. Accordingly, providing the secondary irrigation stem can substantially increase fluid flow rate without otherwise altering the structure of the lens. Yet another purpose for the secondary irrigation stem 64 is to provide a caregiver with two separate irrigation points to introduce different types of irrigating solutions to the eye, and without having to disconnect tubing or remove the ocular lens. For example, a standard irrigation fluid such as saline solution could be used for the primary irrigation stem 38, while antibiotic fluid or a chemically treated fluid could be provided through the secondary stem 64. In this regard, the different treating fluids could be introduced simultaneously. For an antibiotic/chemically treated irrigation fluid, this may be a fluid which needs to be periodically transferred to the eye in relatively small incremental volumes, while a steady flow of irrigation fluid may also be required. In this example, provision of two separate irrigation stem is advantageous because the steady flow of irrigation fluid could be provided through the stem 38 while the treated irrigation fluid can be provided through the secondary stem 64. Another potential purpose for the secondary irrigation stem 64 is that it may also facilitate better delivery of fluid to a different region of the eye. The anatomy of the eye is such that the opening of the eyelids (referred to as the palbebral fissure) extends further down on the side of the eye away from the nose. If the lens is oriented such that the secondary irrigation stem 64 is placed on the side of the eye closest to the nose, additional irrigation can be provided to that particular region of the eye. FIGS. 23-26 also show that the secondary stem 64 serves as a replacement structure for one of the directional fins 36; therefore, the secondary stem 64 serves as a means to keep the ocular lens centered over the eye without materially altering the basic functioning of the ocular lens in terms of how it remains centered over the eye.

Figure 31:
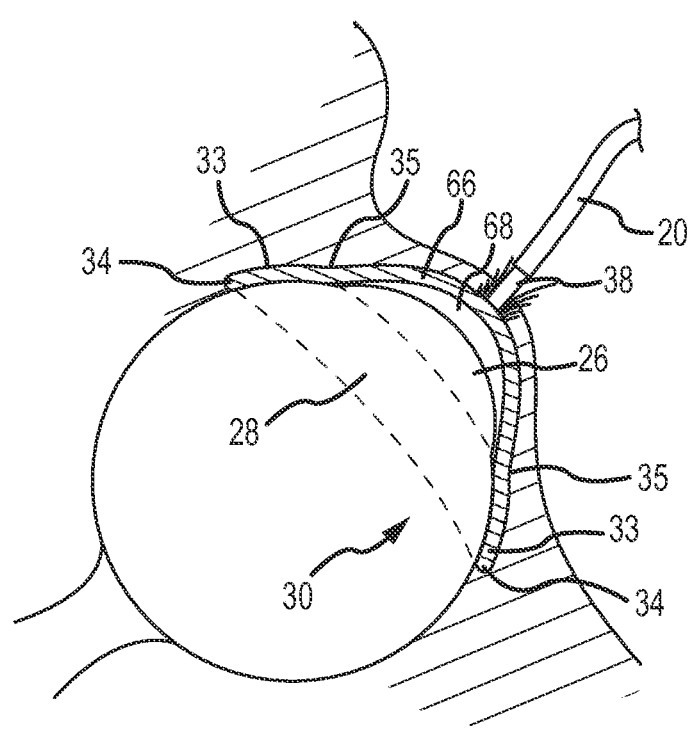
FIG. 31 is an enlarged cross-section of the ocular lens of FIG. 30 showing the lens installed over an eye to be treated.

Referring to FIGS. 27-31, yet another embodiment is illustrated in which the shape of the body 32 is changed to provide a larger gap or space between the interior surface of the lens and the surface of the eye. More specifically, the central convex dome is slightly enlarged and is shown as dome 66. Dome 66 may also have a slightly increased convex curvature. Referring specifically to FIG. 31, the larger gap between the interior surface of the lens and the eye is apparent as compared to the prior art FIG. 2. This increased gap is generally referenced as gap/space 68 in FIG. 31. As with the features of the invention shown in other embodiments, the creation of the increased sized gap 68 has multiple potential purposes. One purpose of the increased gap 68 allows for a larger volume of fluid to be retained between the cornea and the lens without changing the outside dimensions of the lens. A larger sustained volume of fluid within the gap 68 may enhance both the dilution mechanism of action, as well as the flushing mechanism of action. For emergency situations in which it may be necessary to immediately flush a maximum amount of fluid, this embodiment may be particularly advantageous.

According to another embodiment of the invention, the shape of the body 32 can be further modified to provide a dome 66 with a larger diameter so the transition line 35 is moved radially outward and beyond the corneal limbus of the eye. The corneal limbus can be described as the border between the cornea and the sclera. Accordingly, the reservoir of fluid within the gap 68 is enlarged since the dome 66 has a greater diameter. It is also contemplated that the height of the gap 68 does not have to be enlarged as compared to the prior art. In such case, the enlargement of the area defined by the gap 68 is only a function of the dome 66 having a larger diameter, and the curvature of the dome 66 can remain the same as the prior art.

Figure 32:
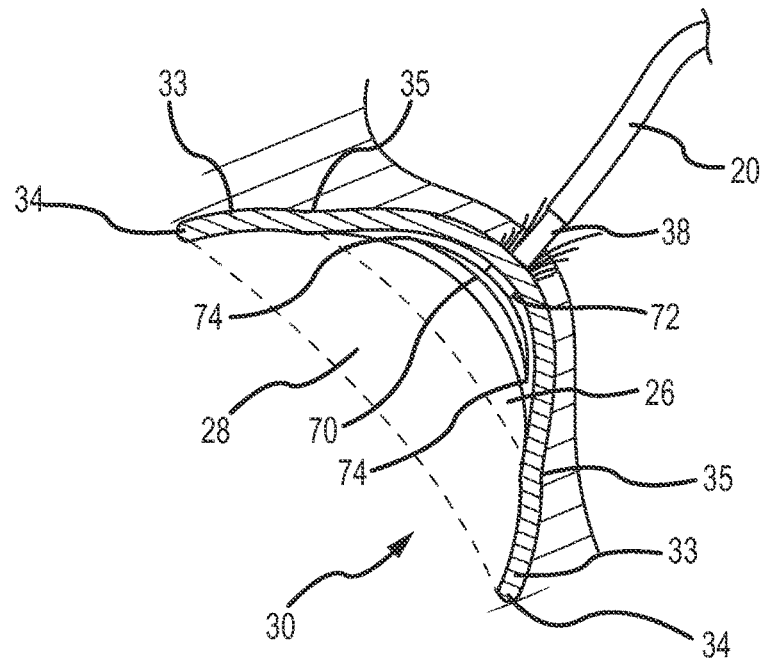
FIG. 32 is an enlarged cross-section of an ocular lens according to another preferred embodiment incorporating a diffusing element, and showing the lens installed over an eye to be treated.

Referring to FIG. 32, yet another embodiment is illustrated which shows the ocular lens 30 with an interior diffusing element 70 for purposes of reducing the velocity of the incoming fluid flow from the irrigation stem 38 and/or for purposes of changing the distribution pattern of the fluid as it contacts the eye. The diffusing element 70 may be circular or oval shaped. Optionally, the diffusing element 70 may have one or more openings (not shown) to change the flow pattern of fluid from the irrigating stem 38. In general, the diffusing element 70 causes the flow of fluid to be spread out over a greater surface area, which may also facilitate greater turbulence for dilution action. According to one preferred embodiment of the diffusing element 70 as shown in FIG. 32, the diffusing element 70 is mounted to the interior surface of the ocular lens with a small flexible connector 72 made of the same material as the ocular lens and/or diffusing element. This flexible connector 72 allows the diffusing element to continually wobble or vibrate as irrigation fluid passed to enhance the turbidity of the fluid flow. As shown, the flexible connector 72 is made of a sufficiently small length and size so the diffusing element 72 is not be capable of contacting the surface of the eye, even under very low irrigation flow rate conditions. The connector may be aligned with the stem 38 in which case an opening(s) may be made through the connector to allow fluid passage, or the connector can be offset from the stem 38 so fluid flows directly from the stem to contact the facing surface of the diffusing element. Another way in which the diffusing element 70 may be secured to the interior surface of the lens 30 is to have selected portions or areas at or near the peripheral edge 74 of the diffusing element attached directly to the interior surface of the lens.

Figure 33:
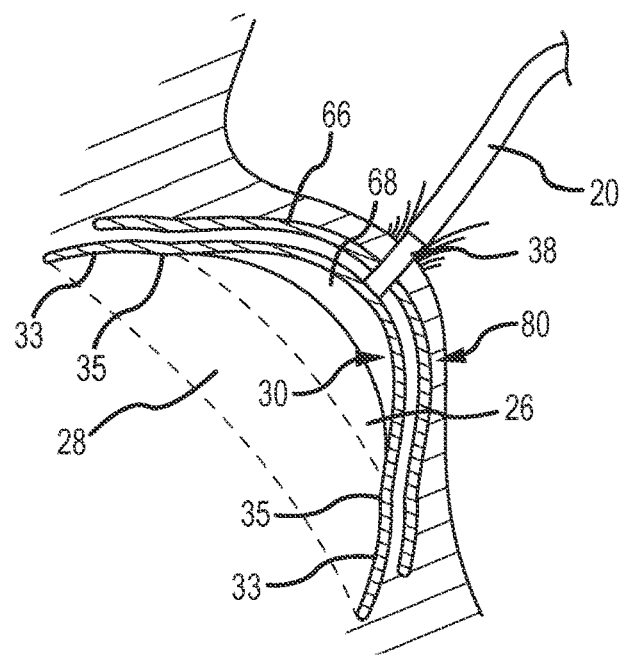
FIG. 33 is an enlarged cross-section of an ocular lens according to another preferred embodiment incorporating a secondary lens, and showing the lens installed over an eye to be treated.

Referring to FIG. 33, yet another embodiment is illustrated which shows the ocular lens 30 with an additional or secondary ocular lens 80. The lenses are placed in a stacked arrangement in which the lenses are separated by attaching the upper lens above the lower lens at a spaced height on the stem 38. As shown, the upper lens is the lens 80 and the lower lens is the lens 30. The shape and size of the lens 80 is substantially the same as the lens 30, the only difference illustrated being the lens 80 having a slightly smaller diameter. The body of the lower lens 30 can be integrally formed with the stem, as the lens 30 is depicted in the other embodiments, and the upper lens 80 is attached only to the stem 38 so that there is a gap between the lenses at the location of the stem 38. FIG. 33 also represents how the lenses may appear when a sufficient flow of irrigation fluid causes the lenses to be separated from one another substantially across the entire gap between the lenses as fluid is allowed to flow within this gap. In this embodiment, each of the ocular lenses may be thinner in cross section so the lens will still fit comfortably within a patient's eye. The lower lens 30 positioned closer to the patient's eye can be either be in a fixed position relative to the upper lens 80, or a selectively movable position relative to the upper lens 80. In the fixed position, the gap between the lenses would remain substantially constant in all directions during irrigation fluid flow. In the selectively movable position, the gap between the lenses would continually change based upon the flow characteristics of the irrigation fluid in which the upper lens would wobble or move in response to flow of the irrigation fluid. The upper lens 80 may have a reduced stiffness or thickness as compared to the lower lens in order to achieve the wobble movement, or may be of a smaller diameter to achieve the movement. One advantage of a dual lens embodiment is similar to the advantages of the above described embodiment utilizing the interior diffusing element. According to another advantage of this embodiment, the selectively movable position may produce a variable flow rate and flow direction of irrigation fluid that may contribute to a more uniform flow of irrigation fluid to each region of the eye. In this regard, any temporary pooling of irrigation fluid or reduced flow rate of irrigation fluid in a particular portion of the eye can be avoided, particularly for low flow rate conditions.

Figure 34:
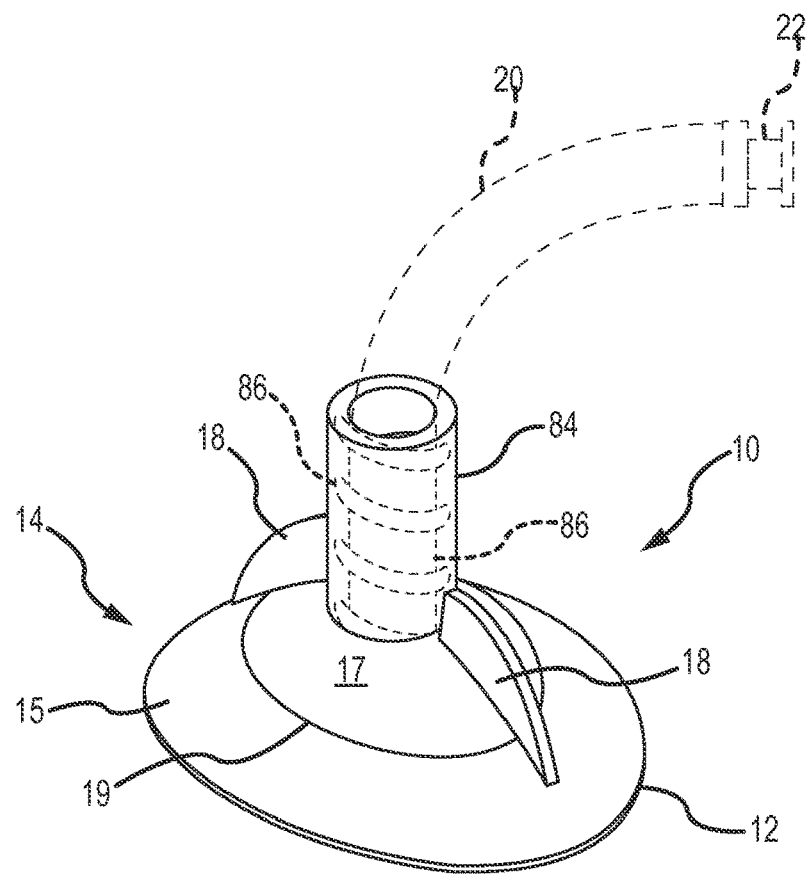
FIG. 34 is an enlarged perspective view of an ocular lens according to another preferred embodiment incorporating a fluid transfer stem with internal channels.
Figure 34A:
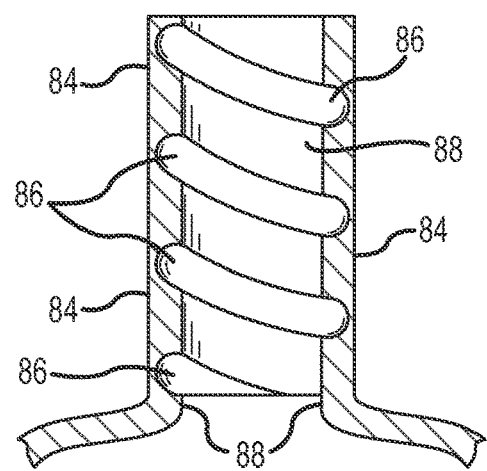
FIG. 34A is an enlarged partial cross section of FIG. 34 showing the internal channels.

Referring to FIGS. 34 and 34A, yet another embodiment is illustrated which shows the use of a modified irrigation stem 84 with an interior surface 88 that generates a vortex flow of irrigation fluid as it flows out from the irrigation stem. More specifically, this embodiment shows a modified irrigation stem 84 with helical arranged flutes or channels 86 formed on the interior surface 88 of the irrigation stem that causes fluid passing through the stem 84 to mix in a vortex type fashion as the fluid exits from the stem. This figure also illustrates that the irrigation stem 84 is slightly larger in diameter and has a greater length/height in order to induce the vortex flow. One advantage of providing the modified irrigation stem 84 is that the velocity of the fluid flow would be reduced in favor of increasing turbulence of the fluid flow in order to improve a mixing action for dilution of caustic contaminants such as chemical or biological agents. Therefore, use of this type of ocular lens may be particularly effective for providing a sustained turbulent flow of irrigation fluid to an eye that may have been traumatized with a caustic contaminant.

Figure 35:
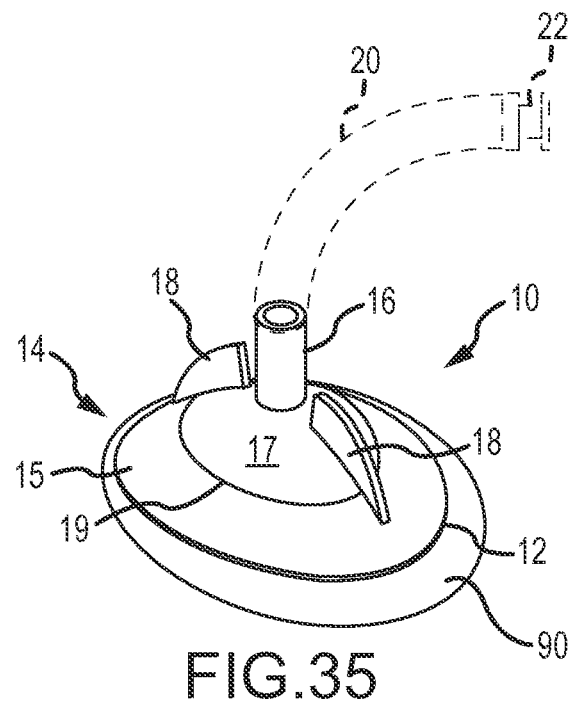
FIG. 35 is a perspective view of an ocular lens according to another preferred embodiment incorporating a peripheral border or skirt.

Referring to FIG. 35, yet another embodiment is illustrated which incorporates the use of a peripheral border or skirt 90 that is added to the peripheral edge of the lens. As shown, the peripheral border 90 increases an overall diameter of the lens, but remains of a size that is still easily inserted in the patient's eye. The peripheral border 90 is thinner in cross section as compared to the other parts of the lens, and is intended to be shown in FIG. 35 as a very thin, flexible member that is gentle on the sclera, yet thick enough to direct irrigating fluid beyond its edges. This embodiment may be effective to distribute irrigation fluid more quickly to corners or depths in the eye that may initially not receive an equal amount of irrigation fluid as compared to exposed surfaces of eye. It is also contemplated that the added peripheral border 90 is thin and flexible enough that it would be capable of moving under the influence of fluid flow, which may also contribute to additional turbulence for dilution purposes. The added peripheral border 90 could be made of the same material as the body of the lens, or could be made of a different material which may be better suited for acting as a very thin membrane to direct fluid flow, but yet maintains adequate flexibility so the peripheral border remains a very nonintrusive expansion of the lens structure.

Figure 36:
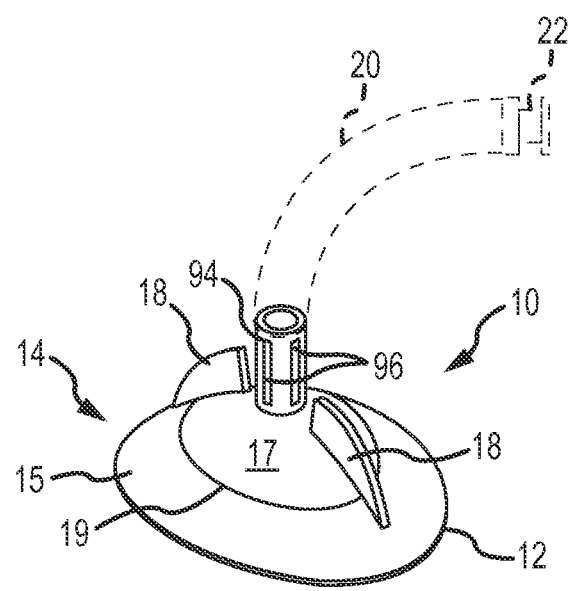
FIG. 36 is a perspective view of an ocular lens according to another preferred embodiment incorporating openings formed on the fluid transfer stem.

Referring to FIG. 36, yet another embodiment is illustrated which incorporates the use of a modified irrigation stem 94 including one or more openings 96 formed along the height of the irrigation stem such that a selected portion of the fluid flowing through the irrigation stem 94 can be directed onto the upper surface of the lens. This embodiment may be particularly advantageous if it is desired to provide more immediate flushing of the inner eyelids without the use of openings made in the body of the lens. The size and directional configuration of the openings 96 in the irrigation stem can be designed so that there is an adequate flow rate of fluid through these openings, and the fluid can be directed in to locations on the eye most advantageous for flushing or irrigating the inner eyelids.

Figure 37:
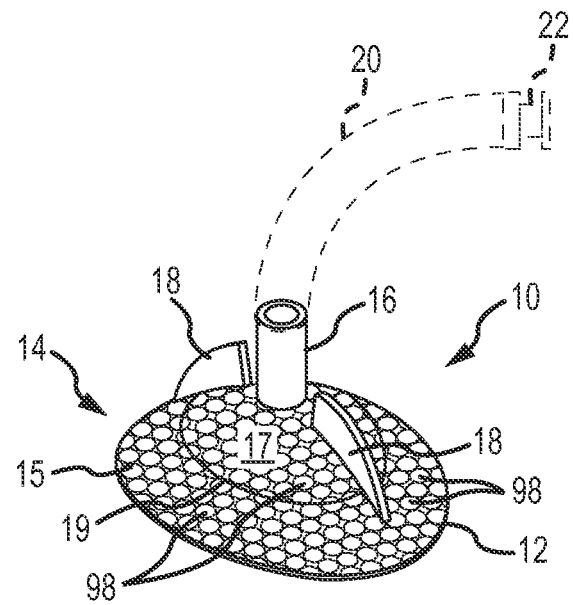
FIG. 37 is a perspective view of an ocular lens according to another preferred embodiment incorporating a surface pattern on one or more surfaces of the lens to adjust fluid flow characteristics of fluid passing over the surfaces.

Referring to FIG. 37, yet another embodiment is illustrated in which the interior or exterior surface of the lens, or both, has/have a dimpled or generally irregular surface pattern 98 formed thereon. The purpose of having the irregular surface pattern 98 is to primarily increase turbulence of the fluid flow thereby improving mixing action for dilution of caustic contaminants. By increasing turbulence, flow velocity of the fluid also generally decreases and therefore, in those applications in which less velocity of fluid flow is advantageous, this embodiment provides corresponding advantage. The specific pattern shown in FIG. 37 shows a surface pattern 98 similar to dimpled pattern of a golf ball. However, it should be understood that there are a multitude of other patterns, both regular and irregular, that could be formed on the interior or exterior surfaces of the lens so that specific fluid flow characteristics could be optimized.

Figure 38:
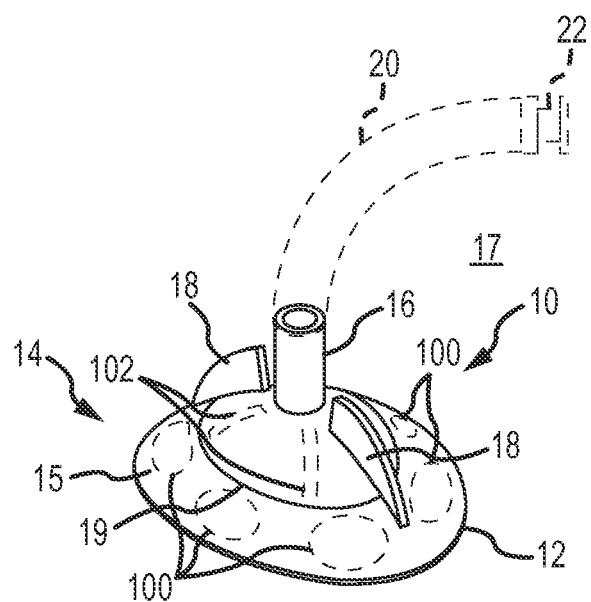
FIG. 38 is a perspective view of an ocular lens according to another preferred embodiment incorporating score lines formed on the body of the lens, the score lines defining locations where openings or channels can be made.

Referring to FIG. 38, yet another embodiment is illustrated in which a plurality of weakened areas defined by score lines are adopted for creating openings in the lens to selectively control fluid flow characteristics. Two types of score lines are illustrated, namely, score lines 100 for creating round openings in the body of the lens 30, or score lines 102 for creating channels or elongated openings in the body of the lens. These two examples are simply representative of the type of channels or openings that may be made in the lens for purposes of fluid flow control. A user could choose to separate and remove selected portions of the lens defined within the score lines to create various flow patterns for fluid flow control. The score lines enable a user to remove the corresponding section of the lens without undue force that may otherwise tear or damage other portions of the lens. For example, a user could separate and remove the desired portion(s) of the lens by hand (with sterile gloves), or by use of a sterile implement. This embodiment of the invention therefore represents a feature enabling a user to selectively control fluid flow characteristics without having to use multiple different lenses of different constructions.

According to other preferred embodiments of the invention, it is contemplated that multiple features can be incorporated within a single ocular lens design. For example, combining the features of the embodiment of FIGS. 11-14 with the features of the embodiment of FIGS. 27-31 may provide a particular advantageous ocular lens design in which increased volume of irrigation fluid flow is provided for both the cornea and the inner surfaces of the eyelids.

According to methods of the invention, an ocular lens is provided with selected structural features to achieve one or more objectives with respect to control of irrigation fluid so that selected portions of the eye and eyelids may be more effectively irrigated or otherwise treated. Control of the irrigation fluid can be described in terms of variables of fluid flow characteristics to include control of flow velocity, flow volume, flow direction, and flow turbidity. Selected structural features of the ocular lens may address one or more of these variables alone or in selected combinations in order to provide an optimal method for treating a patient.

According to one specific aspect of the method, for example, a method may involve altering the body of the lens to provide one or more openings to enable multiple flow directions to include a portion of flow under the interior surface of the lens and a portion of flow over the top or exterior surface of the lens. According to another aspect, a method may involve providing the interior surface of the lens with a uniform or irregular surface pattern in order to change flow characteristics such as flow velocity or flow turbidity. According to yet another example, a method may involve modification of the structure of the irrigation stem in several ways to affect fluid flow characteristics, such as providing openings on a base of the irrigation stem, providing concentric passageways within the irrigating stem, providing the irrigation stem with helical protrusions on the interior surface thereof to generate a vortex flow of fluid, and others. According to yet another example, a method may involve forming passageways through the body of the lens in order to specifically direct fluid flow to desired portions of the patient's eye. According to yet another example, a method may involve increasing the overall size or diameter of the lens by use of a peripheral border in order to more effectively direct fluid flow to corner portions of the eye. According to yet another example, a method may involve changing the curvature of one or more portions of the lens, such as enlarging the central dome of the lens in order to create a larger gap between the patient's eye and the interior surface of the lens, and thereby also altering fluid flow characteristics.

By a review of the foregoing detailed description and drawings, it should be apparent that there are number of features and advantages provided by the invention, both in terms of devices and methods. Further, while the invention has been described with respect to preferred embodiments, it shall be understood that various modifications and changes to the invention can be made commensurate with the scope of the claims appended hereto.

What is claimed is:

1. An ocular lens for irrigation of an eye, comprising:
a body having a shape with a convex curvature, said body further having an interior surface and an exterior surface;
an irrigation stem connected to said body and having a passageway for fluid to pass through said irrigation stem and to enable the fluid to communicate with the interior surface of said body; and
a body feature formed on said body, said body feature including at least one opening formed through said body and spaced from said irrigation stem, said at least one opening enabling the fluid to flow under and over said interior and exterior surfaces to irrigate both a cornea of the eye and inside surfaces of an eyelid of the eye.

2. An ocular lens, as claimed in claim 1, wherein:
said at least one opening includes a plurality of openings spaced from one another on said body.

3. An ocular lens, as claimed in claim 1, wherein:
said at least one opening has a shape selected from at least one of a circular shape, an oval shape, a triangular shape, or combinations thereof.

4. An ocular lens, as claimed in claim 1, wherein:
said at least one opening includes a plurality of openings spaced from one another on said body, and said openings having uniform sizes and shapes.

5. An ocular lens, as claimed in claim 1, wherein:
said at least one opening includes a plurality of openings spaced from one another on said body, and said openings having at least one of different sizes or shapes.

6. An ocular lens, as claimed in claim 1, further including:
at least one directional fin extending from an upper surface of said body.

7. An ocular lens, as claimed in claim 1, wherein:
said body has a central convex portion and an outer circumferential body portion that surrounds said central convex portion, said circumferential body portion having a second different convex curvature.

8. An ocular lens, as claimed in claim 7, wherein:
said at least one opening is formed in said central convex portion.

9. An ocular lens, as claimed in claim 7, wherein:
said at least one opening is formed in said central convex portion and extends to said outer circumferential body portion.

10. An ocular lens, as claimed in claim 7, wherein:
said central convex portion has a first convex curvature and said circumferential body portion has a second different convex curvature.

* * * * *